United States Patent [19]

Goodbar

[11] 4,259,958

[45] Apr. 7, 1981

[54] MULTI-LAYER ABSORBENT PAD FOR DISPOSABLE ABSORBENT ARTICLES AND PROCESS FOR PRODUCING SAME

[75] Inventor: Reid C. Goodbar, Ware Shoals, S.C.

[73] Assignee: Riegel Textile Corporation, Greenville, S.C.

[21] Appl. No.: 46,113

[22] Filed: Jun. 6, 1979

[51] Int. Cl.³ ............................................. A41B 13/02
[52] U.S. Cl. .................................. 128/287; 428/289; 428/301
[58] Field of Search ............... 128/284, 286, 287, 290, 128/296; 428/301

[56] References Cited

U.S. PATENT DOCUMENTS

| Re. 26,939 | 8/1970 | Hervey et al. | 128/284 |
| Re. 28,139 | 8/1974 | Gore | 128/284 |
| 3,017,304 | 1/1962 | Burgeni | 128/290 |
| 3,211,147 | 10/1965 | Pherson et al. | 128/284 |
| 3,554,862 | 1/1971 | Hervey et al. | 128/284 |
| 3,554,863 | 1/1971 | Hervey et al. | 128/284 |
| 3,612,055 | 10/1971 | Mesek et al. | 128/287 |
| 3,768,480 | 10/1973 | Mesek et al. | 128/287 |
| 3,837,343 | 9/1974 | Mesek | 128/287 |
| 3,984,272 | 10/1976 | Teed . | |
| 4,050,462 | 9/1977 | Woon et al. | 128/287 |

Primary Examiner—Robert W. Michell
Assistant Examiner—C. F. Rosenbaum
Attorney, Agent, or Firm—Bell, Seltzer, Park & Gibson

[57] ABSTRACT

Process of forming and resultant multi-layer absorbent pad for use in disposable absorbent articles, such as diapers and the like, to absorb body fluids and being characterized by providing superior fluid transfer from a top uncompressed receiving layer to a bottom compressed layer and wicking and spreading action of the body fluids within the bottom layer to provide a drier top surface to the absorbent pad. The top layer is formed of fiberized cellulosic fibers including a cationic debonding agent provided therein prior to fiberization for obtaining more complete fiberization of the fibers and greater height and loft to the layer while producing resistance to normally-occurring hydrogen bonds between the fibers in the layer to resist compression of the layer and maintain the height and loft of the absorbent pad. The bottom layer is formed of fiberized cellulosic fibers without a cationic debonding agent therein for allowing compression of the layer by effecting the normally-occurring hydrogen bonds between the fibers in the compressed layer to provide a more densified layer for improved fluid wicking and spreading action.

12 Claims, 8 Drawing Figures

MULTI-LAYER ABSORBENT PAD FOR DISPOSABLE ABSORBENT ARTICLES AND PROCESS FOR PRODUCING SAME

Field Of The Invention

This invention relates to a process of producing and the construction of an absorbent pad for use in disposable absorbent articles to absorb body fluids and being characterized by providing superior fluid transfer from a top uncompressed receiving layer to a bottom compressed layer and wicking and spreading action of the body fluids within the bottom compressed area to provide a drier top surface to the absorbent pad. The invention further relates to the process of producing and the construction of a disposable diaper utilizing such improved multi-layer absorbent pad.

BACKGROUND OF THE INVENTION

Disposable absorbent articles, such as disposable diapers, have heretofore conventionally been constructed utilizing a fluid permeable top sheet for being positioned in contact with the wearer for receiving and passing therethrough body fluids, a fluid impermeable bottom sheet positioned away from the wearer for preventing the body fluids of the wearer from passing out of the article and an absorbent pad positioned between the top sheet and the bottom sheet for absorbing the body fluids of the wearer.

Examples of such disposable diaper constructions may be seen in U.S. Pat. No. 3,636,952, issued Jan. 25, 1972, and U.S. Pat. No. 3,951,151, issued Apr. 20, 1976, both of which are assigned to the assignee of the present invention. Processes and apparatus for producing these types of disposable diapers may be seen in U.S. Pat. No. Re 28,139, reissued Aug. 27, 1974 and U.S. Pat. No. 3,984,272, issued Oct. 5, 1976, both of which are assigned to the assignee of the present invention.

As may be seen in these process and apparatus patents, and more particularly in U.S. Pat. No. 3,857,657, issued Dec. 31, 1974, assigned to the assignee of the present invention, the absorbent interior pads for these disposable articles or disposable diapers are conventionally produced by fiberizing a wet-pressed sheet of cellulosic fibers with a "licker-in" type fiberizing means and air laying the fibers to form a batt or pad of individual fiberized fibers. This fiberizing and air-laying mechanism and operation may be utilized directly in the diaper fabricating apparatus and process or it may be separately utilized for forming fiberized fiber batts or pads. Other types of apparatus including "hammer mill" type devices have also been utilized for fiberizing of wet-pressed wood pulp sheets into individual fibers for batts or pads in disposable absorbent articles.

To aid in fiberizing of the wet-pressed cellulosic fiber sheets, which are normally produced by paper manufacturers and provided to disposable articles fabricators, it has heretofore been suggested to utilize or treat the wet-pressed wood pulp sheets and fibers therein with a cationic debonding agent for purposes of aiding in the fiberizing operation and to obtain an air-laid batt or pad of fibers after fiberizing which is substantially completely fiberized and which does not have undesirable residual sheet particles therein, broken fibers and dust, so as to provide greater height and loft to the resulting fiberized fiber batt or pad. Such treatment of fibers during production of a wet-pressed cellulosic fiber sheet with a cationic debonding agent is disclosed in U.S. Pat. No. Re. 26,939, reissued Aug. 18, 1970, U.S. Pat. No. 3,554,862, issued Jan. 12, 1971 and U.S. Pat. No. 3,554,863, issued Jan. 12, 1971, all of which are assigned to the assignee of the present invention.

Although the apparatus, processes and resulting disposable diaper products and fiberized fiber absorbent pads of the above-mentioned prior patents of the assignee of the present invention have been satisfactory and commercially successful to the assignee of the present invention, it has been found that certain problems did exist with respect to providing a top surface on the absorbent pad which would be drier to the wearer of the disposable absorbent article and with respect to wicking and spreading of the body fluids within the absorbent pad away from the top surface of the absorbent pad.

SUMMARY OF THE INVENTION

Accordingly, it is the object of this invention to provide a process of producing and an improved absorbent pad construction to absorb body fluids which is characterized by providing superior fluid transfer from a top surface to a bottom area and wicking and spreading action of the fluids within the bottom area to provide a drier top surface to the absorbent pad, along with a process for producing and a disposable diaper construction utilizing such improved absorbent pad.

By this invention, it has been found that the above object may be accomplished by providing a process of producing and the resultant multi-layer absorbent pad along with a disposable diaper utilizing such improved absorbent pad which is characterized by providing superior fluid transfer from a top receiving layer to a bottom layer and wicking and spreading action of the bottom fluids within the bottom layer to provide a drier top surface to the absorbent pad.

The absorbent pad construction includes a top layer of an uncompressed batt of fiberized cellulosic fibers having a cationic debonding agent therein provided prior to fiberization for obtaining more complete fiberization of the fibers and greater height and loft to the batt while producing resistance to normally-occurring hydrogen bonds between the fibers in the batt to resist compression of the batt and maintain the height and loft for the absorbent pad construction. The absorbent pad further includes a bottom layer comprising a compressed batt or fiberized cellulosic fibers without a cationic debonding agent therein having substantially greater fiber density than said top layer and having normally-occurring hydrogen bonds between the fibers due to the absence of said debonding agent for improved fluid wicking and spreading action. With this construction, body fluids will be received and passed through the uncompressed top layer in a relatively small area thereof and will be wicked and spread out in a larger area of the compressed bottom layer.

This improved multi-layer absorbent pad is preferably utilized in a disposable diaper comprising a fluid permeable top sheet for being positioned in contact with the wearer for receiving and passing therethrough body fluids and a fluid impermeable bottom sheet positioned away from the wearer for preventing the body fluids of the wearer from passing out of the diaper, wherein the multi-layer absorbent pad of this invention is positioned between the top sheet and the bottom sheet for absorbing the body fluids of the wearer.

The disposable diaper utillizing the improved multi-layer absorbent pad of this invention may preferably be of an hour-glass unfolded configuration having a narrower width crotch area and including elastic strips secured to the diaper along outside longitudinal edges at least in the crotch area for forming contractible side portions in the diaper at least in the crotch area for better conformance to the wearer.

In producing the improved multi-layer absorbent pad construction of this invention, the process includes providing a wet-pressed sheet of cellulosic fibers which has not been treated with a cationic debonding agent, mechanically fiberizing the untreated wet-pressed sheet and air-laying the fibers for forming a bottom layer for the multi-layer absorbent pad, providing a wet-pressed sheet of cellulosic fibers treated with a cationic debonding agent, mechanically fiberizing the treated wet-pressed sheet and air-laying the fibers for forming a top layer for the multi-layer absorbent pad which is substantially completely fiberized and which resists compression by providing resistance to the normally-occurring hydrogen bonds between the fibers due to the presence of the cationic debonding agent therein to provide a greater height and loft to the absorbent pad, and compressing the bottom layer of untreated fiberized fibers including effecting the normally-occurring hydrogen bonds between the fibers in the absence of the catinoic debonding agent to provide a more densified layer for greater fluid wicking and spreading action.

Preferably, the compressing step of the process is performed on the superimposed top layer and bottom layer after fiberizing and air-laying of these layers in superimposed conditon, while allowing the top layer to thereafter return substantially to its uncompressed state due to resistance to compression therein by resistance to the normally-occurring hydrogen bonds between the fibers because of the presence of the cationic debonding agent therein to provide a greater height and loft to the absorbent pad for fluid transfer therethrough and the bottom layer to remain compressed due to effecting of the normally-occurring hydrogen bonds between the fibers in the absence of the cationic debonding agent to provide a more densified layer for greater fluid wicking and spreading action.

The step of compressing may preferably comprise embossing to form a predetermined pattern of embossed areas within the bottom for further aiding in the wicking and spreading action.

BRIEF DESCRIPTION OF THE DRAWINGS

Some of the objects and advantages of this invention having been set forth, other objects and advantages will appear when taken in conjunction with the accompanying drawings, in which.

DETAILED DESCRIPTION OF INVENTION

In the drawings, FIGS. 1-6 illustrate a disposable diaper 10 which is the preferred disposable absorbent article for utilizing the improved multi-layer absorbent pad 20 of this invention. It is to be understood, however, that the improved absorbent pad 20 of this invention could also be utilized in other disposable absorbent articles.

Generally, the disposable diaper 20 comprises a fluid permeable top sheet 11 which may be of any suitable construction conventionally utilized in disposable diaper and other absorbent article constructions for being positioned in contact with the wearer of the disposable diaper 10 for receiving and passing therethrough body fluids of the wearer. The disposable diaper 10 further includes a fluid impermeable bottom sheet 12 which may be constructed of plastic or other suitable material conventionally utilized in such disposable diaper and other disposable absorbent article constructions for being positioned away from the wearer for preventing the body fluids of the wearer from passing out of the disposable diaper 10 or other disposable absorbent article. The improved multi-layer absorbent pad 20 of this invention is positioned between the top sheet 11 and bottom sheet 12 for absorbing the body fluids of the wearer. The disposable diaper 10 is secured along its longitudinal and transverse edges by any suitable glue or other adhesive attachment means 14 which secures the top sheet 11 to the bottom sheet 12 and generally provides an envelope around the interior pad 20.

Figure 1:
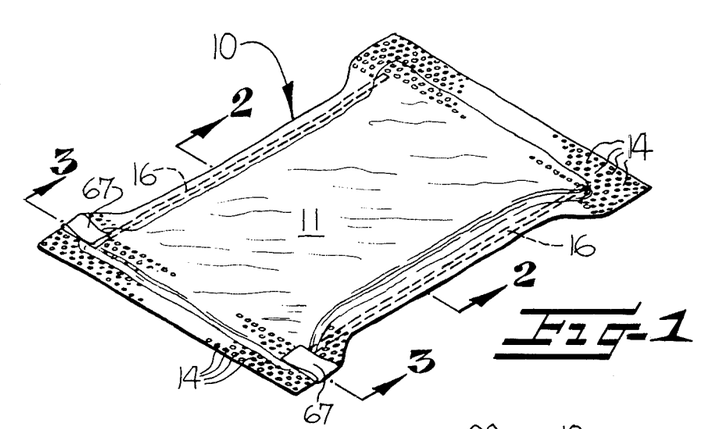
FIG. 1 is a perspective view of a disposable diaper utilizing the improved multi-layer absorbent pad of the present invention and in its flat condition wherein the elastic strips on the longitudinal edges thereof are in their extended condition.
Figure 2:
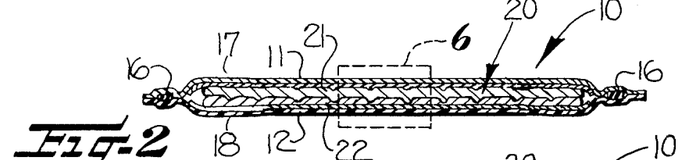
FIG. 2 is a sectional view, taken generally along the line 2—2 of FIG. 1.
Figure 3:
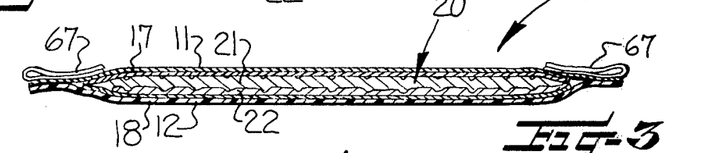
FIG. 3 is a sectional view, taken generally along the line 3—3 of FIG. 1.
Figure 4:
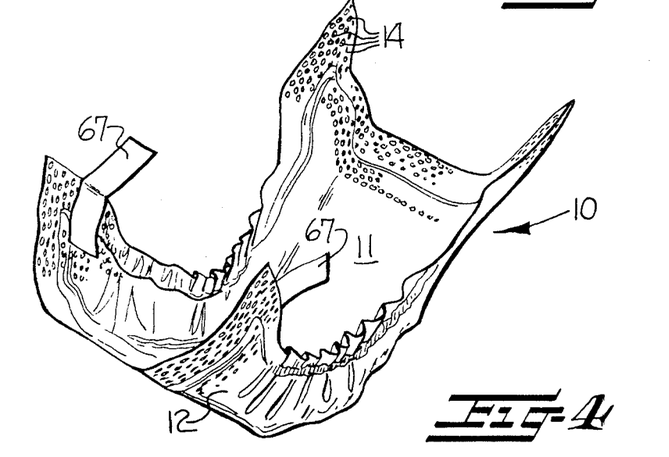
FIG. 4 is a view of the disposable diaper of FIG. 1 in the relaxed condition of the elastic strips along the longitudinal side edges of the diaper.

Preferably, the disposable diaper 10 defines a generally hour-glass unfolded flat configuration, as illustrated in FIG. 1, having a narrower width crotch area or portion for placement around the crotch of the wearer and elastic strips 16 secured to the diaper 10 along the outside longitudinal edges thereof at least in the crotch area for forming contractible side portions in the diaper 10 at least in the crotch area, as illustrated in FIG. 4, for better conformance to the wearer. These elastic strips 16 may be secured along the longitudinal edges by being placed between the top sheet 11 and bottom sheet 12 and glued or otherwise secured in place by the adhesive means 14.

The improved multi-layer absorbent pad construction 20 of this invention comprises a top layer 21 composed of an uncompressed batt of fiberized cellulosic fibers having a cationic debonding agent therein provided prior to fiberization, in accordance with the above-identified U.S. Patents of the assignee of the present invention, for obtaining a more complete fiberization of the fibers and greater height and loft to the batt while producing resistance to normally-occurring hydrogen bonds between the fibers in the batt to resist compression of the batt and maintain height and loft of the absorbent pad 20.

As is well understood by those with ordinary skill in the art, cellulosic fibers have a natural affinity to each other by normally-occurring hydrogen bonds between the cellulosic fiber molecules when pressed or forced together. Further explanation of this concept which is inherent in all paper-making art is not believed necessary for a full understanding of the present invention. However, when the cellulosic fibers are treated with a cationic debonding agent, in accordance with the above-identified U.S. Patents of the assignee of the present invention, the cationic debonding agent provides a resistance to these normally-occurring hydrogen bonds between the cellulosic fibers for purposes of aiding in fiberizing of the fibers and which after fiberization presents a resistance to further effecting the normally-occurring hydrogen bonds between fibers and therefore a resistance to compression of a batt of such fiberized fibers which maintains height and loft of a batt of such fibers.

The improved multi-layer absorbent pad construction 20 further comprises a bottom layer 22 composed of a compressed batt of fiberized cellulosic fibers without a cationic debonding agent therein for allowing compression of the batt by effecting the above-discussed normally-occurring hydrogen bonds between the fibers in the compressed batt to provide a more densified batt for improved fluid wicking and spreading action.

Figure 5:
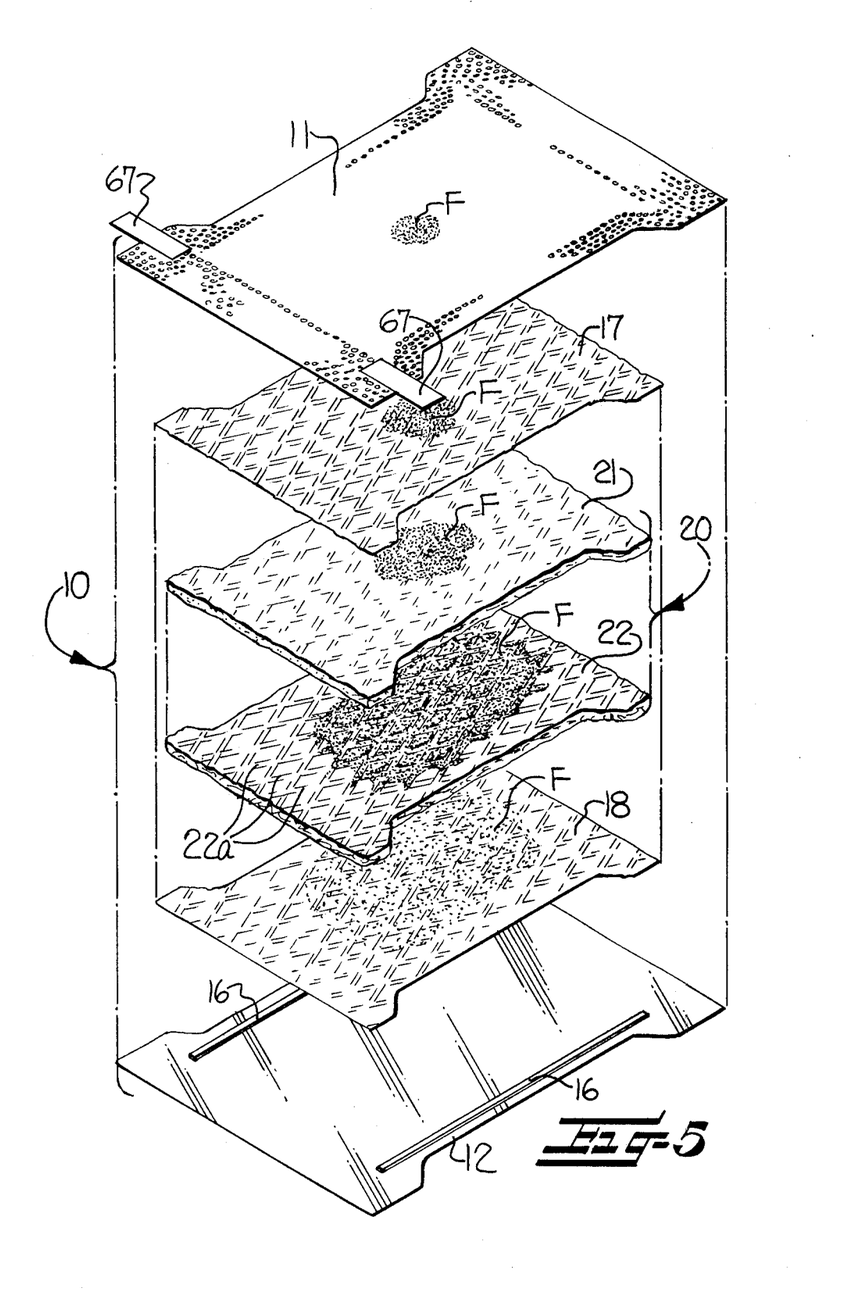
FIG. 5 is an exploded view of the disposable diaper of FIG. 1 illustrating the components thereof.

With the above construction of a multi-layer absorbent pad 20, body fluids F may be received and passed through the uncompressed top layer 21 in a relatively small area indicated schematically at F in FIG. 5, and will be wicked and spread out in a larger area of the compressed bottom layer 22, as also indicated schematically at F in FIG. 5. It is well known to those with ordinary skill in the art fluid will be received and passed through a less dense, more open and lofty, uncompressed layer of fibers and will be wicked and spread out in a more densified compressed layer of fibers. Accordingly, a further explanation of this action is not deemed necessary for an understanding of this invention.

Preferably, the compressed bottom layer 22 of fiberized cellulosic fibers without a cationic debonding agent therein further comprises an embossed batt of fibers defining a predetermined pattern of embossed areas 22a within the layer 22 for further aiding in wicking and spreading action of the body fluids by being more compressed and more densified than the remaining portions of the compressed bottom layer 22, as may be seen schematically in FIG. 5.

The disposable diaper 10 may further include a sheet or crepe cellulosic wadding 17 disposed between the top sheet 11 and the multi-layer absorbent pad 20 and a sheet of crepe cellulosic wadding 18 disposed between the bottom sheet 12 and the multi-layer absorbent pad 20, as may be seen particularly in FIG. 5, for stabilizing the pad 20. These sheets of crepe cellulosic wadding 17, 18 may be of conventional construction normally utilized in disposable diapers or other absorbent articles.

Figures 6, 7:
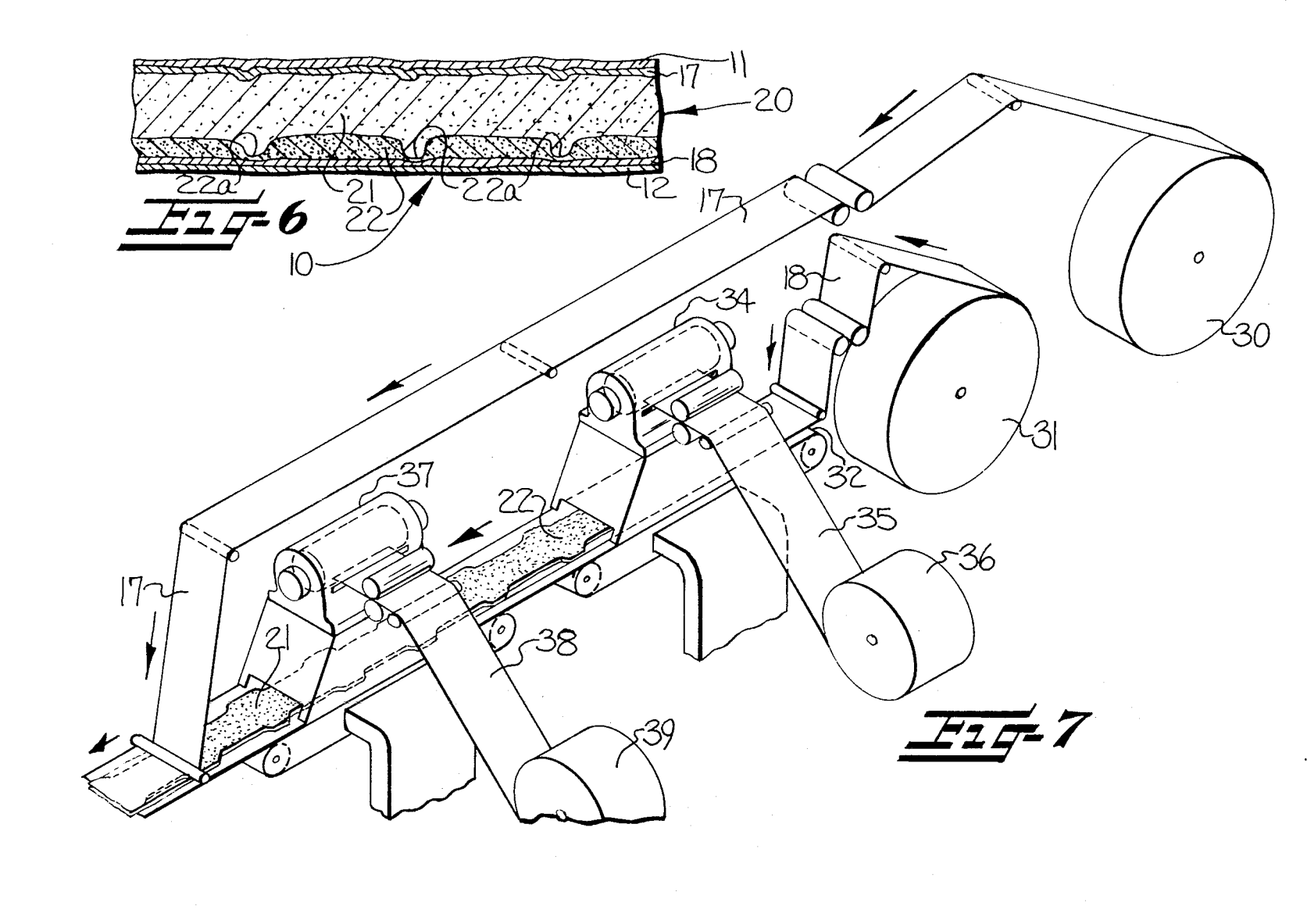
FIG. 6 is an elarged sectional detail of a portion of the disposable diaper, taken generally within the rectangle 6 of FIG. 2.
FIGS. 7 and 8 are continuation views schematically illustrating apparatus for practicing the process of forming a disposable diaper utilizing the improved absorbent pad construction of this invention.
Figure 8:
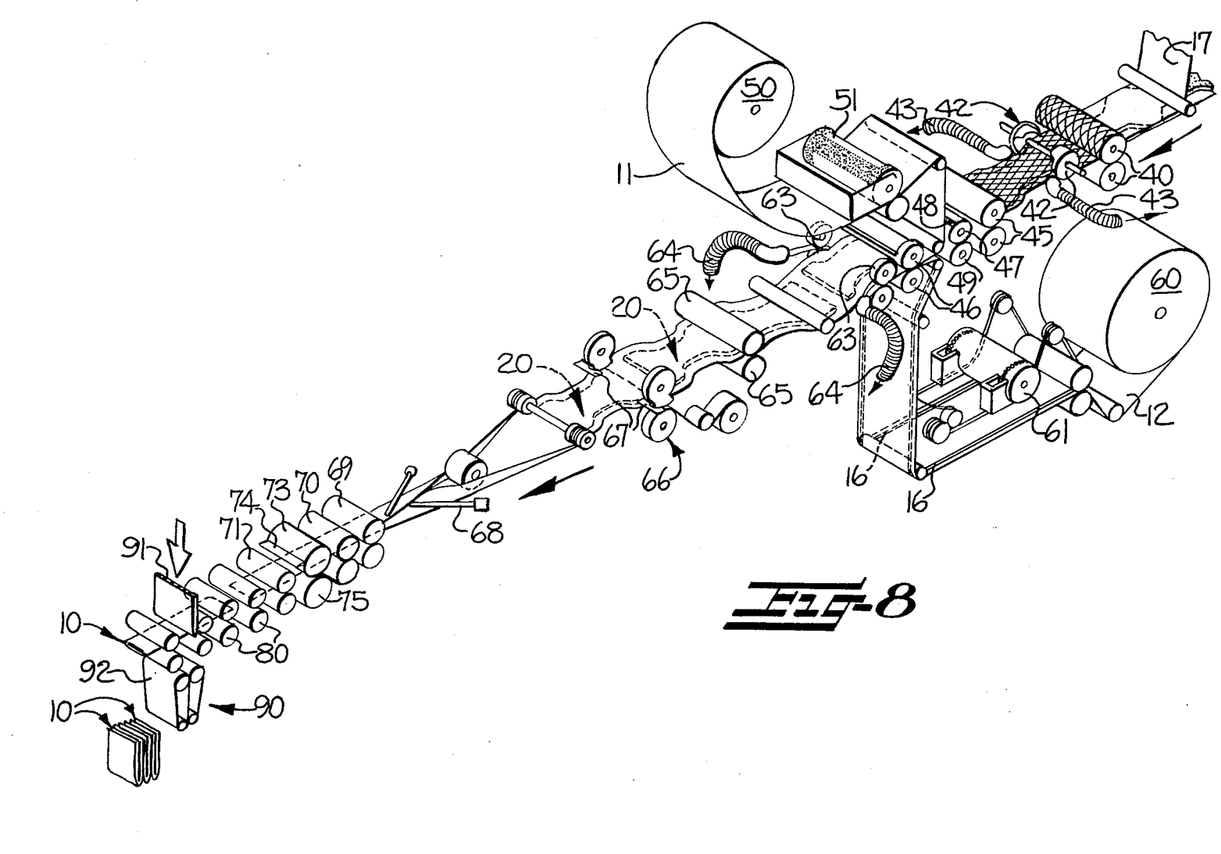

Referring now to FIGS. 7 and 8 of the drawings, there is schematically illustrated therein an apparatus suitable for performing the processes of this invention. It is to be understood, however, that other apparatus may be utilized in performing the novel processes of this invention.

As illustrated in FIGS. 7 and 8, sources of supply 30, 31 are provided for the respective sheet of crepe cellulosic wadding 17, 18. As may be seen, the bottom sheet of crepe cellulosic wadding 18 is fed from its source of supply 31 onto a moving conveyor belt 32. This conveyor belt 32 moves through a first fiberizing and air-laying apparatus 34 which may be constructed in accordance with assignee's aforementioned U.S. Pat. Nos. 3,857,657. This fiberizing and air-laying apparatus 34 receives a sheet of untreated wet-pressed wood pulp fibers 35 from a suitable supply source 36 and fiberizes the sheet 35 into individual fibers and air-lays the fibers into a bottom layer 22 on top of the sheet of crepe cellulosic wadding 18 being carried on the conveyor 32. As may be seen in FIG. 7, the bottom layer 22 is formed in a plurality of interconnected generally hour-glass configurations for forming a multiplicity of interconnected pads 20.

The thus formed layer 22 and bottom crepe cellulosic wadding sheet 18 are then fed to a conveyor 41 which forms a part of a second fiberizing and air-laying mechanism 37 which may be constructed like the first fiberizing and air-laying mechanism 34. This second fiberizing and air-laying mechanism 37 receives a sheet of treated wet-pressed wood pulp fibers 38 from a suitable supply source 39 which has been treated with a cationic debonding agent and mechanically fiberizes this wet-pressed cellulosic fiber sheet and air-lays the fibers for forming a top layer 21 for the interconnected multi-layer absorbent pads 20 which is substantially completely fiberized due to the presence of the cationic debonding agent therein and which is superimposed on the bottom layer 22. The top sheet of crepe cellulosic wadding 17 is then fed on top of the superimposed fiber layers 21, 22 and bottom crepe cellulosic wadding sheet 18 to form a series of interconnected multi-layer absorbent pads 20.

These interconnected multi-layer absorbent pads 20 are then fed through a pair of embossing rollers 40 which compress the interconnected multi-layer absorbent pads 20 by applying compressing forces to both the top layer 21 and bottom layer 22. Upon leaving the embossing rolls 40, the top layer 21 returns substantially to its uncompressed state due to resistance to compression therein by resistance to the normally-occurring hydrogen bonds between the fibers because of the presence of the cationic debonding agent therein to provide greater height and loft to the absenbent pads 20 for fluid transfer there-through and the bottom layer 22 remains compressed due to effecting of the normally-occurring hydrogen bonds between the fibers in the absence of the cationic debonding agent to provide a more densified layer for greater fluid wicking and spreading action. The embossing rolls 40 form even more compressed and densified areas 22a in the bottom layer 22 in a predetermined pattern according to the pattern on the embossing rolls.

Thereafter, the interconnected multi-layer absorbent pads 20 are fed through edge trimming devices 42 which intermittently trim the edges of the top and bottom sheets of crepe cellulosic wadding 17, 18 into the generally hour-glass configuration of the interconnected absorbent pads 20. Vacuum removal devices 43 may be provided for removing the trimmed material.

The thus formed interconnected multi-layer absorbent pads 20 are then fed through two sets of feed rolls 45, 46 between which is provided pad severing means in the form of a rotating cutter roll 47 having a knife blade 48 thereon and an anvil roll 49 which operate to intermittently cut the interconnected multi-layer pads 20 transversely for separation of the interconnected pads 20. The feed rolls 46 are driven somewhat faster than the feed rolls 45 to effect an overfeeding of the severed multi-layer absorbent pads 20 for spacing the pads 20 apart in the further fabrication of disposable diapers 10.

Immediately prior to the feed rolls 46, the top cover sheet 11 is fed from a suitable source of supply 50 through a glue roll applicator device 51 which applies glue or adhesive 14 in a predetermined pattern transversely across the cover sheet 11 at spaced locations and along the longitudinal edges of the top cover sheet 11 for purposes of gluing the transverse and longitudinal edges of the ultimately fabricated disposable diapers together, as shown in FIG. 1. The top cover sheet 11 with adhesive 14 thereon is then fed into superimposed position on top of the separated multi-layer absorbent pads 20.

Simultaneously, the bottom cover sheet 12 is fed from a suitable source of supply 60 through a suitable device schematically illustrated at 61 for adhesively attaching the elastic strips 16 to each longitudinal edge of the bottom cover sheet 12 at spaced locations thereon which ultimately form the crotch portions of the fabricated disposable diapers 10. The bottom cover sheet 12 with elastic strips 16 thereon is then fed into superimposed position under the separated multi-layer absorbent pads 20 and is pressed into contact with the top cover sheet 11 with adhesive 14 thereon by the feed rolls 46 so as to adhesively secure the top cover sheet 11 and bottom cover sheet 12 to each other along the longitudinal edges and transversely between the separated and spaced absorbent pads 20 to form interconnected disposable diapers 10.

The thus formed interconnected diapers 10 are fed through an edge trimming device 63 which trims the longitudinal edges of the adhesively connected top cover sheet 11 and bottom cover sheet 12 to the desired hour-glass configuration. Vacuum removal means 64 may also be provided with these edge trimming devices 63 for removal of the trimmed material.

The thus formed interconnected diapers 10 are then fed through a pair of feed rolls 65 and past an adhesive tab applying mechanism 66 which applies adhesive tabs 67 at spaced locations on the interconnected diapers 10 for well known purposes in securing the individual diapers to the wearer.

The thus formed interconnected diapers 10 are then fed through a longitudinal folding mechanism 68 for folding the interconnected diapers 10 along longitudinal fold lines into a desired folded configuration. From the folding mechanism 68, interconnected diapers are fed through a series of pairs of feed rolls 69, 70 and 71 between which is disposed a transverse cutting mechanism composed of a cutting roll 73 having a blade 74 thereon and an anvil roll 75 for rotating to cut the interconnected diapers transversely through the transverse adhesively connected portions between spaced-apart interior absorbent pads 20 to form individual separated diapers 10. The thus formed and separted diapers 10 are then fed between a series of guide rolls 80 which are in loose nipping contact with the individual diapers 10, but which do not provide a tight nipping action and allow the diapers to relax to the configuration shown generally in FIG. 4. Between these guide rolls 80 there is disposed a transverse or center fold mechanism 90 having a folding blade 91 adapted to engage the separated individual diapers 10 transversely across their mid-point and move the diapers downwardly between a set of belt conveyors 92 for forming individual folded diapers 10 which may be fed to any suitable packaging station.

Thus, the apparatus illustrated in FIG. 7 may be utilized for the improved process of this invention of producing disposable diapers 10 having an improved multi-layer absorbent pad construction 20 therein to absorb body fluids F and provide superior fluid transfer from a top uncompressed receiving layer 21 to a bottom compressed layer 22 and wicking and spreading action of the body fluids F within the bottom compresssed layer 22 to provide a drier top surface or top cover sheet 11 to the absorbent pad and diaper construction.

This process comprises generally the steps of producing multi-layer absorbent pads 20 comprising providing a wet-pressed sheet 35 of cellulosic fibers which has not been treated with a cationic debonding agent, mechanically fiberizing the untreated wet-pressed sheet 35 and air-laying the fibers for forming a bottom layer 22 for the multi-layer absorbant pads 20, feeding the thus formed bottom layer 22 along a longitudinal path of travel, providing a wet-pressed sheet 38 of cellulosic fibers treated with a cationic debonding agent, mechanically fiberizing the treated wet-pressed sheet 38 and air-laying the fibers onto the bottom layer 22 as the bottom layer 22 is being fed in its longitudinal path of travel for forming a top layer 21 for the multi-layer absorbent pads 20 which is substantially completely fiberized due to the presence of the cationic debonding agent therein, and compressing the multi-layer absorbent pads 20 by applying compressing forces to both the top layer 21 and the bottom layer 22 and thereafter allowing the top layer 21 to return substantially to its uncompressed state due to resistance to compression therein by resistance to the normally-occurring hydrogen bonds between the fibers because of the presence of the cationic debonding agent therein to provide greater height and loft to the absorbent pads 20 for fluid transfer therethrough and the bottom layer 22 to remain compressed due to effecting of the normally-occurring hydrogen bonds between the fibers in the absence of the cationic debonding agent and provide a more densified layer for greater fluid wicking and spreading action.

The process further includes supplying and positioning an elongate fluid-permeable top cover sheet 11 on top of the absorbent pads 20 and an elongate fluid-impervious bottom cover sheet 12 under the absorbent pads 20, feeling the superimposed top cover sheet 11, interior absorbent pads 20 and bottom cover sheet 12 along a predetermined longitudinal path of travel, transversely securing the top cover sheet 11 and bottom cover sheet 12 together at longitudinally spaced intervals between absorbent pads to form successively interconnected diapers, securing the top cover sheet 11 and bottom cover sheet 12 together along longitudinal side edges, and transversely severing the successively interconnected diapers 10 along the successive transverse securements to form individual diapers 10.

Thus, this invention has provided a process of producing an improved absorbent pad construction 20 to absorb body fluids which is characterized by providing superior fluid transfer a top surface to a bottom area and wicking and spreading action of the fluids within the bottom area to provide a drier top surface to the absorbent pad 20, along with a process of producing a disposable diaper construction 10 utilizing such improved absorbent pad 20.

In the drawings and specification, there have been set forth preferred embodiments of the invention, and although specific terms are employed, they are used in a generic and descriptive sense only and not for purposes of limitation.

What is claimed is:

1. A multi-layer absorbent pad construction for use in disposable absorbent articles, such as diapers and the like, to absorb body fluids and comprising superimposed top and bottom layers operatively associated with each other and being characterized by providing superior fluid transfer from said top receiving layer to said bottom layer and wicking and spreading action of the body fluids within said bottom layer to provide a drier top surface to said absorbent pad;

said top layer comprising an uncompressed batt of fiberized cellulosic fibers having a cationic debonding agent therein provided prior to fiberization for obtaining more complete fiberization of said fibers and greater height and loft to said batt while producing resistance to normally-occurring hydrogen bonds between said fibers in said batt to resist compression of said batt and maintain the height and loft for said absorbent pad construction; and said bottom layer comprising a compressed batt of fiberized cellulosic fibers without a cationic debonding agent therein having substantially greater fiber density than said top layer and having normally-occurring hydrogen bonds between said fibers due to the absence of said debonding agent for improved fluid wicking and spreading action;

whereby, body fluids will be received and passed through said uncompressed top layer in a relatively small area thereof and will be wicked and spread out in a larger area of said compressed bottom layer.

2. A multi-layer absorbent pad construction, as set forth in claim 1, in which said bottom layer comprising a compressed batt of fiberized cellulosic fibers without a cationic debonding agent therein further comprises embossed areas of a predetermined pattern within said layer for further aiding in the wicking and spreading action of the body fluids.

3. A disposable diaper comprising a fluid permeable top sheet for being positioned in contact with the wearer for receiving and passing therethrough body fluids, a fluid impermeable bottom sheet positioned away from the wearer for preventing the body fluids of the wearer from passing out of said diaper, and a multi-layer absorbent pad positioned between said top sheet and said bottom sheet for absorbing the body fluids, said top sheet, said bottom sheet and said absorbent pad being operatively connected together to form a disposable diaper, said absorbent pad comprising superimposed top and bottom layers characterized by providing superior fluid transfer from said top sheet through said top layer to said bottom layer and wicking and spreading action of the body fluids within said bottom layer to provide a drier top sheet in contact with the wearer;

said top layer comprising an uncompressed batt of fiberized cellulosic fibers having a cationic debonding agent therein provided prior to fiberization for obtaining more complete fiberization of said fibers and greater height and loft to said batt while producing resistance to normally-occurring hydrogen bonds between said fibers in said batt to resist compression of said batt and maintain the height and loft for said absorbent pad; and said bottom layer comprising a compressed batt of fiberized cellulosic fibers without a cationic debonding agent therein having substantially greater fiber density than said top layer and having normally -occurring hydrogen bonds between said fibers due to the absence of said debonding agent for improved fluid wicking and spreading action;

whereby, body fluids will be received and passed through said top sheet and said uncompressed top layer of said absorbent pad in a relatively small area thereof and will be wicked and spread out in a larger area of said compressed bottom layer of said absorbent pad.

4. A disposable diaper defining a generally hour-glass unflolded configuration having a narrower width crotch area and including elastic strips secured to said diaper along outside longitudinal edges at least in said crotch area for forming contractible side portions in said diaper at least in said crotch area for better conformance to the wearer and comprising a fluid permeable top sheet for being positioned in contact with the wearer for receiving and passing therethrough body fluids, a fluid impermeable bottom sheet positioned away from the wearer for preventing the body fluids of the wearer from passing out of said diaper, and a multi-layer absorbent pad positioned between said top sheet and said bottom sheet for absorbing the body fluids said top sheet, said bottom sheet and said absorbing pad being operatively connected together to form a disposable diaper, said absorbent pad comprising superimposed top and bottom layers characterized by providing superior fluid transfer from said top sheet through said top layer to said bottom layer and wicking and spreading action of the body fluids within said bottom layer to provide a drier top sheet in contact with the wearer;

said top layer comprising an uncompressed batt of fiberized cellulosic fibers having a cationic debonding agent therein provided prior to fiberization for obtaining more complete fiberization of said fibers and greater height and loft to said batt while producing resistance to normally-occurring hydrogen bonds between said fibers in said batt to resist compression of said batt and maintain the height and loft for said absorbent pad; and said bottom layer comprising a compressed batt of fiberized cellulosic fibers without a cationic debonding agent therein having substantially greater fiber density than said top layer and having normally-occurring hydrogen bonds between said fibers due to the absence of said debonding agent for improved fluid wicking and spreading action;

whereby, body fluids will be received and passed through said top sheet and said uncompressed top layer of said absorbent pad in a relatively small area thereof and will be wicked and spread out in a larger area of said compressed bottom layer of said absorbent pad.

5. A disposable diaper, as set forth in claim 3 or 4, in which said bottom layer of said multi-layer absorbent pad further comprises an embossed batt of fiberized cellulosic fibers defining a predetermined pattern of embossed areas therein for further enhancing the fluid wicking and spreading action.

6. A disposable diaper as set forth in claim 3 or 4, further including a sheet of crepe cellulosic wadding disposed between said top sheet and said multi-layer absorbent pad and a sheet of crepe cellulosic wadding disposed between said bottom sheet and said multi-layer absorbent pad for stabilizing said pad.

7. Process of producing a superimposed multi-layer absorbent pad construction for use in disposable articles, such as diapers and the like, to absorb body fluids and providing superior fluid transfer from a top uncompressed receiving layer to a bottom compressed layer and wicking and spreading action of the body fluids within the bottom compressed layer to provide a drier top surface to the absorbent pad; said process comprising the steps of:
- providing a wet-pressed sheet of cellulosic fibers which has not been treated with a cationic debonding agent;
- mechanically fiberizing the untreated wet-pressed sheet and air-laying the fibers for forming a bottom layer for the multi-layer absorbent pad;
- providing a wet-pressed sheet of cellulosic fibers treated with a cationic debonding agent;
- mechanically fiberizing the treated wet-pressed sheet and air-laying the fibers for forming a top layer for the multi-layer absorbent pad which is substantially completely fiberized and which resists compression by providing resistance to the normally-occurring hydrogen bonds between the fibers due to the presence of the cationic debonding agent therein to provide a greater height and loft to the absorbent pad; and
- compressing the bottom layer of untreated fiberized fibers including effecting the normally occurring hydrogen bonds between the fibers in the absence of the cationic debonding agent to provide a more densified layer for greater fluid wicking and spreading action.

8. Process of producing a multi-layer absorbent pad contruction for use in disposable articles, such as diapers and the like, to absorb body fluids and providing superior fluid transfer from a top uncompressed receiving layer to a bottom compressed layer and wicking and spreading action of the body fluids within the bottom compressed layer to provide a drier top surface to the absorbent pad; said process comprising the steps of
- providing a wet-pressed sheet of cellulosic fibers which has not been treated with a cationic debonding agent;
- mechanically fiberizing the untreated wet-pressed sheet and air-laying the fibers for forming a bottom layer for the multi-layer absorbent pad;
- providing a wet-pressed sheet of cellulosic fibers treated with a cationic debonding agent;
- mechanically fiberizing the treated wet-pressed sheet and air-laying the fibers onto the bottom layer for forming a top layer for the multi-layer absorbent pad which is substantially completely fiberized due to the presence of the cationic debonding agent therein; and
- compressing the multi-layer absorbent pad by applying compressing forces to both the top layer and the bottom layer and thereafter allowing the top layer to return substantially to its uncompressed state due to resistance to compression therein by resistance to the normally-occurring hydrogen bonds between the fibers because of the presence of the cationic debonding agent therein to provide a greater height and loft to the absorbent pad for lfuid transfer therethrough and the bottom layer to remain compressed due to effecting of the normally-occurring hydrogen bonds between the fibers in the absence of the cationic debonding agent to provide a more densified layer for greater fluid wicking and spreading action.

9. Process of producing a multi-layer absorbent pad construction, as set forth in claim 7 or 8, in which said step of compressing comprises
- embossing to form a predetermined pattern of embossed areas within the bottom layer for further aiding in the wicking and spreading action of the body fluids.

10. Process of producing disposable diapers having an improved multi-layer absorbent pad construction therein to absorb body fluids and providing superior fluid transfer from a top uncompressed receiving layer to a bottom compressed layer and wicking and spreading action of the body fluids within the bottom compressed layer to provide a drier top surface to the absorbent pad; said process comprising the steps of:
- producing multi-layer absorbent pads comprising providing a wet-pressed sheet of cellulosic fibers which has not been treated with a cationic debonding agent, mechanically fiberizing the untreated wet-pressed sheet and air-laying the fibers for forming a bottom layer for the multi-layer absorbent pads, feeding the thus formed bottom layer along a longitudinal path of travel, providing a wet-pressed sheet of cellulosic fibers treated with a cationic debonding agent, mechanically fiberizing the treated wet-pressed sheet and air-laying the fibers onto the bottom layer as the bottom layer is being fed in its longitudinal path of travel for forming a top layer for the multi-layer absorbent pads which is substantially completely fiberized due to the presence of the cationic debonding agent therein, and compressing the multi-layer absorbent pads by applying compressing forces to both the top layer and the bottom layer and thereafter allowing the top layer to return substantially to its uncompressed state due to resistance to compression therein by resistance to the normally-occurring hydrogen bonds between the fibers because of the presence of the cationic debonding agent therein to provide greater height and loft to the absorbent pads for fluid transfer therethrough and the bottom layer to remain compressed due to effecting of the normally-occurring hydrogen bonds between the fibers in the absence of the cationic debonding agent to provide a more densified layer for greater fluid wicking and spreading action;
- supplying and positioning an elongate fluid-permeable top cover sheet on top of the absorbent pads and an elongate fluid-impervious bottom cover sheet under the absorbent pads;
- feeding the superimposed top cover sheet, interior absorbent pads and bottom cover sheet along a predetermined longitudinal path of travel;
- transversely securing the top cover sheet and the bottom cover sheet together at predetermined longitudinally spaced intervals between absorbent pads to form successively interconnected diapers;
- securing the top cover sheet and bottom cover sheet together along longitudinal side edges; and
- transversely severing the successively interconnected diapers along the successive transverse securement to form individual diapers.

11. Process of producing disposable diapers, as set forth in claim 10, further including
- forming the disposable diapers in a generally hourglass unfolded configuration having narrower width crotch areas, and
- providing and securing elastic strips to the diapers along outside longitudinal edges at least in the crotch areas for forming contractible side portions in the diapers at least in the crotch areas for better conformance to the wearer.

12. Process of producing a disposable diaper, as set forth in claim 10, in which
said step of compressing the multi-layer absorbent pads comprises:
embossing the multi-layer absorbent pads to form a predetermined pattern of embossed areas in the bottom layer of the absorbent pads for further enhancing the fluid wicking and spreading action.

* * * * *

UNITED STATES PATENT AND TRADEMARK OFFICE
CERTIFICATE OF CORRECTION

PATENT NO. : 4,259,958
DATED : April 7, 1981
INVENTOR(S) : Reid C. Goodbar

It is certified that error appears in the above-identified patent and that said Letters Patent are hereby corrected as shown below:

Assignee's location should be "Greenville, South Carolina", instead of New York, New York.

Column 2, line 36, "bottom" (first occurrence) should be --body--
Column 3, line 27, "catinoic" should be --cationic--
Column 3, line 33, "conditon" should be --condition--
Column 4, line 62, after "maintain" insert --the--
Column 5, line 31, after "art" insert --that--
Column 6, line 1, "Nos." should be --No.--
Column 6, line 41, "absenbent" should be --absorbent--
Column 6, line 42, "there-through" should be --therethrough--
Column 7, line 54, "separted" should be --separated--
Column 8, line 5, "compresssed" should be --compressed--
Column 8, line 42, "feeling" should be --feeding--
Column 8, line 56, after "transfer" insert --from--
Column 9, line 66, "mally -occurring" should be --mally-occurring--
Column 11, line 22, "normally occurring" should be --normally-occurring--
Column 11, line 58, "lfuid" should be --fluid--.

Signed and Sealed this

Twenty-third Day of June 1981

[SEAL]

Attest:

RENE D. TEGTMEYER

Attesting Officer

Acting Commissioner of Patents and Trademarks